(12) United States Patent
Su

(10) Patent No.: US 10,071,201 B2
(45) Date of Patent: Sep. 11, 2018

(54) DISEASE TESTING AND THERAPEUTIC DEVICE AND REMOTE MONITORING SHOES

(71) Applicant: Bo Su, Qingdao (CN)

(72) Inventor: Bo Su, Qingdao (CN)

( * ) Notice: Subject to any disclaimer, the term of this patent is extended or adjusted under 35 U.S.C. 154(b) by 887 days.

(21) Appl. No.: 14/396,005

(22) PCT Filed: Oct. 22, 2013

(86) PCT No.: PCT/CN2013/085637
§ 371 (c)(1),
(2) Date: Oct. 21, 2014

(87) PCT Pub. No.: WO2014/114115
PCT Pub. Date: Jul. 31, 2014

(65) Prior Publication Data
US 2015/0088057 A1 Mar. 26, 2015

(30) Foreign Application Priority Data

Jan. 22, 2013 (CN) .......................... 2013 1 0022938
Jan. 22, 2013 (CN) ..................... 2013 2 0032527 U

(51) Int. Cl.
*A61M 5/172* (2006.01)
*A61M 5/20* (2006.01)
(Continued)

(52) U.S. Cl.
CPC ......... *A61M 5/1723* (2013.01); *A43B 3/0005* (2013.01); *A61B 5/02055* (2013.01);
(Continued)

(58) Field of Classification Search
CPC .. A61M 5/1723; A61M 5/007; A61M 5/1424; A61M 5/1428; A61M 5/14586;
(Continued)

(56) References Cited

U.S. PATENT DOCUMENTS 6,281,594 B1 * 8/2001 Sarich ...................... A43B 3/00
290/1 A
6,836,744 B1 12/2004 Asphahani et al.
(Continued)

FOREIGN PATENT DOCUMENTS

CN 101107025 A 1/2008
CN 201067121 Y 6/2008
(Continued)

*Primary Examiner* — Emily Schmidt
*Assistant Examiner* — Alexandra Lalonde
(74) *Attorney, Agent, or Firm* — Jiwen Chen

(57) ABSTRACT

The invention discloses a detection and therapeutic device and remote monitoring shoes. The detection and therapeutic device comprises a power supply module (a) which is connected with modules with electricity needs and used for powering the modules, a main processor module (b) which is used for collecting and processing signals from sensors and controlling working status of an automatic injection module (d), a detection sensor module (c) which comprises a plurality of sensors in connection with the main processor module (b) and is used for examining nerves, organs or secretions and sending back the results to the main processor module (b), an automatic injection module (d) which comprises a plurality of automatic injectors in connection with the main processor module (b) and is used for administrating according to signals for controlling from the main processor module automatically.

18 Claims, 9 Drawing Sheets

(51) Int. Cl.
*A61B 5/00* (2006.01)
*A43B 3/00* (2006.01)
*A61B 5/0205* (2006.01)
*A61B 5/145* (2006.01)
*A61F 7/00* (2006.01)
*A61M 5/145* (2006.01)
*H02K 7/116* (2006.01)
*H02K 35/02* (2006.01)
*H02K 7/18* (2006.01)
*A61B 5/021* (2006.01)
*A61M 5/142* (2006.01)
*A61M 5/14* (2006.01)

(52) U.S. Cl.
CPC ...... *A61B 5/14532* (2013.01); *A61B 5/14546* (2013.01); *A61B 5/4839* (2013.01); *A61B 5/6807* (2013.01); *A61B 5/746* (2013.01); *A61F 7/00* (2013.01); *A61F 7/007* (2013.01); *A61M 5/1452* (2013.01); *A61M 5/20* (2013.01); *H02K 7/116* (2013.01); *H02K 7/1892* (2013.01); *H02K 35/02* (2013.01); *A61B 5/021* (2013.01); *A61F 2007/0045* (2013.01); *A61F 2007/0071* (2013.01); *A61F 2007/0088* (2013.01); *A61F 2007/0093* (2013.01); *A61F 2007/0095* (2013.01); *A61M 5/14* (2013.01); *A61M 5/14244* (2013.01); *A61M 2005/14252* (2013.01); *A61M 2005/14272* (2013.01); *A61M 2005/206* (2013.01); *A61M 2205/0272* (2013.01); *A61M 2205/3553* (2013.01); *A61M 2205/3561* (2013.01); *A61M 2205/3569* (2013.01); *A61M 2205/3584* (2013.01); *A61M 2205/3606* (2013.01); *A61M 2205/825* (2013.01); *A61M 2205/8281* (2013.01); *A61M 2210/086* (2013.01); *A61M 2230/06* (2013.01); *A61M 2230/201* (2013.01); *A61M 2230/208* (2013.01); *A61M 2230/30* (2013.01); *A61M 2230/50* (2013.01)

(58) Field of Classification Search
CPC .............. A61M 5/14593; A61M 5/148; A61M 5/1483; A61M 5/1486; A61M 5/152; A61M 2205/82; A61M 2205/825; A43B 3/0005; A43B 3/0015; A43B 3/00; A43B 13/20; A43B 13/203; A43B 7/04; H02K 7/116; H02K 7/18; A61B 5/00; B60K 6/08; B60K 6/10; B60K 6/12; B60L 11/16

See application file for complete search history.

(56) References Cited

U.S. PATENT DOCUMENTS

| | | | | |
|---|---|---|---|---|
| 8,013,463 | B2* | 9/2011 | Preston | ..................... F03G 7/00 290/1 R |
| 2008/0127510 | A1* | 6/2008 | Yang | ....................... A43B 3/00 36/29 |
| 2008/0287832 | A1 | 11/2008 | Collins et al. | |
| 2010/0063438 | A1* | 3/2010 | Bengtsson | ........ A61M 5/14248 604/66 |
| 2011/0178359 | A1* | 7/2011 | Hirschman | ............ A61B 6/037 600/4 |
| 2013/0033042 | A1* | 2/2013 | Fortier | ................. A43B 3/0015 290/54 |
| 2014/0145450 | A1* | 5/2014 | Stanton | ................ H02K 7/1853 290/1 C |

FOREIGN PATENT DOCUMENTS

| | | |
|---|---|---|
| CN | 101392735 A | 3/2009 |
| CN | 101711121 A | 5/2010 |
| CN | 201519339 U | 7/2010 |
| FR | 2861846 A1 | 5/2005 |

* cited by examiner

DISEASE TESTING AND THERAPEUTIC DEVICE AND REMOTE MONITORING SHOES

CROSS-REFERENCE TO RELATED ALLOCATIONS

This is the National Stage filing under 35 U.S.C. 371 of the International Application PCT/CN2013/08563 filed Oct. 22, 2013, which claims priority under 35 U.S.C. 119 (a-d) to CN201310022938, filed Jan. 22, 2013 and CN201320032527, filed Jan. 22, 2013.

FIELD OF THE TECHNOLOGY

The present invention relates to health technology, particularly to a detection and therapeutic device and remote monitoring shoes paired with the detection and therapeutic devices.

BACKGROUND OF THE INVENTION

In the prior art, detection or health examination is normally conducted at a fixed time and at a fixed site by professionals with medical devices. It is quite difficult for individuals to test on their own at any time and any place, let alone the achievement of automatic therapies or treatment. Due to the facts that health status cannot be detected by patients themselves, potential risk factors for health are hard to be perceived timely for precaution or treatment. Furthermore, the victim or people nearby cannot be informed of signs of sudden illness to give first aid as emergencies, such as sudden cardiovascular and cerebrovascular disease or dizziness caused by hypoglycemia occurs. Lives of patients are put at serious risks.

SUMMARY OF THE INVENTION

One of the objects of the present invention is to provide a detection and therapeutic device. The detection and therapeutic device is small in size, portable, and capable of monitoring health status of users at any time and implementing automatic treatments as sudden illnesses occur.

In order to achieve the object, the detection and therapeutic device adopts technical solutions as follows.

The detection and therapeutic device comprises:
a power supply module which is connected with modules with electricity requirements of the detection and therapeutic device and used for powering the modules;
a main processor module which is used for collecting and processing signals from a plurality of sensors and controlling working status of an automatic administration module;
a detection sensor module comprises a plurality of detection sensors and every sensor is connected with the main processor module. The detection sensor module is used for inspecting nerves, organs or secretions and sending back the results to the main processor module; and
an automatic administration module comprises automatic injectors and the automatic injector is connected with the main processor module and used for administrating automatically according to signals for controlling from the main processor module.

In order to send out the results produced by the sensors and/or receive external health guiding information and the like, the detection and therapeutic device further comprises a wireless signal transmission module which is connected with the main processor module and the power supply module and used for receiving or sending out wireless signals.

In order to timely warn the victim or others about the monitored potential risk factors for health, the detection and therapeutic device further comprises an alarming module which is connected with the main processor module and the power supply module and used for sending out warning signals, a heating module and/or cooling module which are or is connected with the main processor module, so that users could keep warm or lower body temperature as required.

In order to reduce energy consumption, the detection and therapeutic device preferably adopts a self power-generating working approach. Accordingly, the power supply module comprises a self-generating power unit and an electrical energy storage unit which is connected with the self-generating power unit and used for storing electrical energy. The modules with electricity requirements of the detection and therapeutic device are respectively connected with the power output of the self-generating power unit and the power output of the electrical energy storage unit.

The self-generating power unit comprises stroke rods, mechanical energy accumulators which are drivingly connected with the stroke rods, electrical generators which are connected with the mechanical energy accumulators and a rectifier which is connected with the electrical generators.

The stroke rod comprises a rod body, a piston ring and a stroke wheel arranged inside the rod body, gasbags which are used for driving the piston ring to move vertically are positioned between the piston ring and the bottom cap of the rod body, wherein the piston ring is hinged to the stroke wheel by connecting rods. The top cap of the rod body is connected with the top end of the stroke wheel by a tension spring and a stroke axle penetrating through the rod body is arranged in the middle part of the stroke wheel. One end of the stroke axle is embedded inside a groove formed in the rod body and the other end of the stroke axle protrudes from the rod body and is provided with a ratchet wheel. The mechanical energy accumulator comprises a box body, wherein clockwork boxes provided with a clockwork and a transmission shaft are arranged on the lateral sides of the box body. The transmission shaft is used as the power input of the mechanical energy accumulator, wherein one end of the transmission shaft is positioned inside the box body and the other end of the transmission shaft protrudes from the box body and provided with a driven wheel engaging with the ratchet wheel arranged on the stroke axle. Each clockwork box is drivingly connected with an output shaft of the mechanical energy accumulator by the gear transmission mechanism, so as to transmit power to the electrical generator through the output shaft. Electrical energy is sent out to the rectifier after being transformed from mechanical energy by the electrical generator.

The detection and therapeutic device comprises at least one sensor selected from the group of weight sensors, body temperature sensors, blood pressure sensors, pulse rate sensors, blood uric acid sensors, blood glucose sensors, antistreptolysin O sensors, pH value sensors and protein sensors, so as to detect health indicators at any time and at any place.

In order to measure blood pressure and pulse rate, the detection and therapeutic device comprises a gasbag and a telescopic mechanism which is connected with the gasbag, wherein the blood pressure sensor and the pulse rate sensor are positioned on the gasbag.

Further, the telescopic mechanism comprises a hydraulic cylinder, wherein the piston rod of the hydraulic cylinder and the gasbag are in a rigid connection and a hydraulic pump is connected with the cylinder body of the hydraulic cylinder.

Further, the automatic injector of the automatic administration module can be realized in a structure described as follows.

The automatic injector comprises a shell, wherein a syringe with an extruding needle and a needle protective cover are arranged inside the shell and an orifice formed at the position of the needle correspondingly. The syringe is connected with the inner wall of the shell by retaining springs and displacement electromagnetic systems which are used for driving the syringe to move to the orifice are positioned on the syringe. A propelled plate is arranged inside the syringe and a cavity for injection is formed between the end of the inner wall of the syringe with the needle and one side of the propelled plate, and the other side of the propelled plate is connected with an injection electromagnetic system used for driving the propelled plate to move.

The displacement electromagnetic system comprises two sub systems. Each sub system is respectively arranged on one side of the syringe. The sub system comprises an electromagnet arranged on the shell and an iron core inside the electromagnet is wrapped by electromagnetic coils. An attracting arm is positioned below the electromagnet, wherein one end of the attracting arm is hinged to the electromagnet and the other end of the attracting arm is hinged to the syringe. Iron capable of attracting the iron core of the electromagnet according to the current in the electromagnetic coils is arranged on the attracting arm corresponding to the position of the iron core.

The injection electromagnetic system can be achieved as follows: a first propelled plate track and a second propelled plate track are arranged on the side of the propelled plate against the cavity for injection. The injection electromagnetic system comprises an electromagnet fixed on the inner wall of the syringe and the iron core of the electromagnet is wrapped by electromagnetic coils. The injection electromagnetic system is further comprises iron capable of attracting the iron core of the electromagnet according to the electricity current in the electromagnetic coils, a first iron track and a second iron track which enable the iron to slide. One end of the iron positioned on the first iron track is hinged to one end of a first connecting rod mechanism, the other end of the first connecting rod mechanism rolls along the first propelled plate track through a first rolling wheel; the other end of the iron positioned on the second iron track is hinged to one end of a second connecting rod mechanism, the other end of the second connecting rod mechanism rolls along the second propelled plate track through a second rolling wheel.

The automatic injector in the automatic administration module can be further achieved in a structure as follows.

The automatic injector comprises a syringe, a propelled plate arranged inside the syringe, a hook-shaped needle positioned at the front end of the syringe and a cavity for injection is formed between the propelled plate and the end of the inner wall of the syringe with the hook-shaped needle. The automatic injector further comprises an injection electromagnetic system capable of driving the propelled plate and the syringe to move obliquely so as to enable the hook-shaped needle to hook backwards. The injection electromagnetic system comprises a fixed magnet and a moving magnet which are respectively wrapped by electromagnetic coils, wherein both ends of the fixed magnet are hinged to both ends of the syringe away from the tail end of the hook-shaped needle by connecting rods. The iron core of the moving magnet covers the iron core of the fixed magnet and moves along the moving direction of the propelled plate inside the syringe and the front end of the moving magnet is an inclined plane which tilts the propelled plate and the syringe upon the iron core moving towards the propelled plate and contacting with the propelled plate.

The present invention is further aimed at providing remote monitoring shoes. People can be informed of health status automatically at any time and at any place conveniently and give first aid as diseases, particularly sudden diseases occur by wearing the remote monitoring shoes provided with the detection and therapeutic devices.

In order to achieve the above-identified objectives, the remote monitoring shoes can be realized by adopting the technical solutions as follows.

Remote monitoring shoes comprise shoe heels, front shoe soles, shoe uppers and vamps and are characterized in that the detection and therapeutic devices are arranged inside the remote monitoring shoe. The power supply module and the main processor module of each detection and therapeutic device are arranged inside the shoe heels and multiple sensors are positioned dispersedly inside the shoe heels, the front shoe soles and the shoe uppers. The automatic injectors are dispersedly arranged inside the shoe heels and the front shoe soles and the shoe heels are further provided with wireless signal transmission modules respectively connected with the main processor modules and the power supply modules.

The shoe heels are further provided with alarming modules connected with the main processor modules and the power supply modules, so as to warn the users when potential risk factors for health are detected. The front shoe soles are further provided with heating modules connected with the main processor modules and the power supply modules. The shoe uppers are further provided with cooling modules connected with the main processor modules and the power supply modules so as to automatically enable the users to keep cooling or lower body temperature as required.

In order to reduce energy consumption, the remote monitoring shoes preferably adopt a solution that the electrical power consumed is generated by walking with the remote monitoring shoes. In particular, the power supply modules comprise self-generating power units and energy storage units connected with the self-generating power units. The modules with electricity requirements of the detection and therapeutic device are respectively connected with the power output of the self-generating power units and the power output of the electrical energy storage units.

The self-generating power unit comprises stroke rods, mechanical energy accumulators which are drivingly connected with the stroke rods, electrical generators which are connected with the mechanical energy accumulator and a rectifier which is connected with the electrical generators.

The stroke rod comprises a rod body. A piston ring and a stroke wheel are arranged inside the rod body, gasbags which are used for driving the piston ring to move vertically are positioned between the piston ring and the bottom cap of the rod body, wherein the piston ring is hinged to the stroke wheel by connecting rods. The top cap of the rod body is connected with the top end of the stroke wheel by a tension spring and a stroke axle penetrating through the rod body is arranged in the middle part of the stroke wheel. One end of the stroke axle is embedded inside a groove formed in the rod body and the other end of the stroke axle protrudes from the rod body and is provided with a ratchet wheel. The mechanical energy accumulator comprises a box body, wherein clockwork boxes provided with a clockwork and a transmission shaft are arranged on the lateral sides of the box body. The transmission shaft is used as the power input of the mechanical energy accumulator, wherein one end of the transmission shaft is positioned inside the box body and the other end of the transmission shaft protrudes from the box body and provided with a driven wheel engaging with the ratchet wheel arranged on the stroke axle. Each clockwork box is drivingly connected with an output shaft of the mechanical energy accumulator by the gear transmission mechanism, so as to transmit power to the electrical generator through the output shaft. Electrical energy is sent out to the rectifier after being transformed from mechanical energy by the electrical generator.

The remote monitoring shoes are provided with weight sensors inside the shoe heels and the front shoe soles, body temperature sensors, blood uric acid sensors, blood glucose sensors, antistreptolysin O test sensors, pH value sensors and protein sensors inside the front shoe soles and blood pressure sensors and pulse rate sensors on the back ends of the shoe uppers which correspond to the ankle artery, so that health indicators can be detected at any time and at any place.

In order to measure blood pressure and pulse rate for convenience, gasbags and telescopic mechanisms connected with the gasbags are positioned at the rear ends of the shoe uppers and the blood pressure sensors and the pulse rate sensors are arranged on the gasbags.

Further, the telescopic mechanism comprises a hydraulic cylinder, wherein the piston rod of the hydraulic cylinder and the gasbags are in a rigid connection and a hydraulic pump is connected with the cylinder body of the hydraulic cylinder.

The automatic injectors of the automatic administration module arranged inside the remote monitoring shoes can be achieved in a structure as follows.

The automatic injectors are arranged inside the shoe heels and each automatic injector comprises a shell, wherein a syringe with an extruding needle and a needle protective cover are arranged inside the shell and an orifice formed at the position of the needle correspondingly. The syringe is connected with the inner wall of the shell by retaining springs and displacement electromagnetic systems which are used for driving the syringe to move to the orifice are positioned on the syringe. A propelled plate is arranged inside the syringe and a cavity for injection is formed between the end of the inner wall of the syringe with the needle and one side of the propelled plate, and the other side of the propelled plate is connected with an injection electromagnetic system used for driving the propelled plate to move.

Further, the displacement electromagnetic system comprises two sub systems. Each sub system is respectively arranged on one side of the syringe. The sub system comprises an electromagnet arranged on the shell and an iron core inside the electromagnet is wrapped by electromagnetic coils. An attracting arm is positioned below the electromagnet, wherein one end of the attracting arm is hinged to the electromagnet and the other end of the attracting arm is hinged to the syringe. Iron capable of attracting the iron core of the electromagnet according to the electricity current in the electromagnetic coils is arranged on the attracting arm corresponding to the position of the iron core.

The injection electromagnetic system can be achieved as follows: a first propelled plate track and a second propelled plate track are arranged on the side of the propelled plate against the cavity for injection. The injection electromagnetic system comprises an electromagnet fixed on the inner wall of the syringe and the iron core of the electromagnet is wrapped by electromagnetic coils. The injection electromagnetic system is further comprises iron capable of attracting the iron core of the electromagnet according to the electricity current in the electromagnetic coils, a first iron track and a second iron track which enable the iron to slide. One end of the iron positioned on the first iron track is hinged to one end of a first connecting rod mechanism, the other end of the first connecting rod mechanism rolls along the first propelled plate track through a first rolling wheel; the other end of the iron positioned on the second iron track is hinged to one end of a second connecting rod mechanism, the other end of the second connecting rod mechanism rolls along the second propelled plate track through a second rolling wheel.

The automatic injector in the automatic administration module can be further achieved in a structure as follows.

The automatic injector is arranged inside the front shoe soles and comprises a syringe, a propelled plate arranged inside the syringe, a hook-shaped needle positioned at the front end of the syringe and a cavity for injection is formed between the propelled plate and the end of the inner wall of the syringe with the hook-shaped needle. The automatic injector further comprises an injection electromagnetic system capable of driving the propelled plate and the syringe to move obliquely so as to enable the hook-shaped needle to hook backwards. The injection electromagnetic system comprises a fixed magnet and a moving magnet which are respectively wrapped by electromagnetic coils, wherein both ends of the fixed magnet are hinged to both ends of the syringe away from the tail end of the hook-shaped needle by connecting rods. The iron core of the moving magnet covers the iron core of the fixed magnet and moves along the moving direction of the propelled plate inside the syringe and the front end of the moving magnet is an inclined plane which tilts the propelled plate and the syringe upon the iron core moving towards the propelled plate and contacting with the propelled plate.

In order to measure exercise loads of users who wear the remote monitoring shoes according to the results produced by the automatic measurement of walking distance and steps, infrared signal generators and infrared signal receivers which are connected with the main processor modules are arranged on the inner sides of the shoe uppers at intervals.

Compared with the prior art, the present invention has the advantages and positive results in that: the detection and therapeutic device can be used independently and also can be paired with household goods, such as shoes and the like; indicators such as blood pressure, blood glucose, pulse rate and the like which can reflect health status can be detected by the detection sensor module arranged inside the detection and therapeutic device at any time for convenience and can be processed by the main processor module to provide the users with useful health information. Rescue medication, such as heart tonic pills, drugs to lower blood glucose and the like can be administrated automatically by the automatic administration module controlled by the main processor module as the occurrence of diseases, particularly sudden diseases detected by the main processor module so as to provide a strong guarantee of health for users. Users can be warned by the alarming module when risk factors for health are detected. Users can evaluate health status by receiving information processed by the main processor module and sent by the wireless signal transmission module and information of medical care, precaution and treatment can be provided to users so as to further reduce risk factors for health.

Combining with drawings below, other features and advantages of the present invention are demonstrated more clearly in detailed embodiments.

DETAILED EMBODIMENTS OF THE INVENTION

Combining with the drawings and detailed procedures, technical solutions of the present invention are clearly interpreted as follows.

Figure 1:
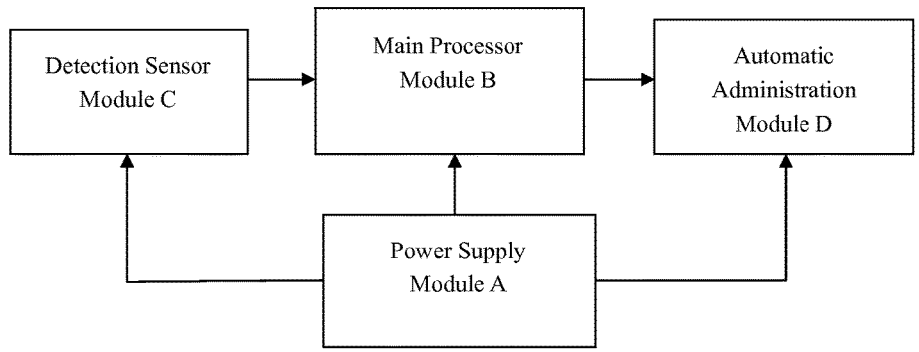
FIG. 1 is a flow chart of the basic principle of the first embodiment of the detection and therapeutic device according to the present invention.

As shown in the FIG. 1, a detection and therapeutic device comprises a power supply module (a), a main processor module (b), a detection sensor module (c) and an automatic administration module (d), wherein:

The power supply module (a) is used for providing energy to the detection and therapeutic device and connected with the modules with electricity requirement thereof. The power supply module (a) can be achieved by adopting storage batteries charged by an external power supply, and also can be achieved by utilizing a self-generating structure powered by mechanical energy or solar energy.

Serving as the core of the detection and therapeutic device, the main processor module (b) is used for collecting and processing signals produced by sensors in the detection sensor module (c) and controlling the working status of the automatic administration module (d). The main processor module (b) can be realized by micro processors as microcontrollers and peripheral circuits thereof.

The detection sensor module (c) comprises a plurality of sensors, wherein every sensor is connected with the main processor module (b), and further connected with the power supply module (a) if electricity power is required. The detection sensor module is used for inspecting nerves, organs or secretions, such as artery, dander and perspiration and sending back the results to the main processor module.

The automatic administration module (d) comprises a plurality of automatic injectors and each of the automatic injectors is respectively connected with the main processor module (b) and the power supply module (a). The automatic administration module is used for administrating automatically according to the signals sent by the main processor module (b) so as to provide first aid through administration.

Figure 2:
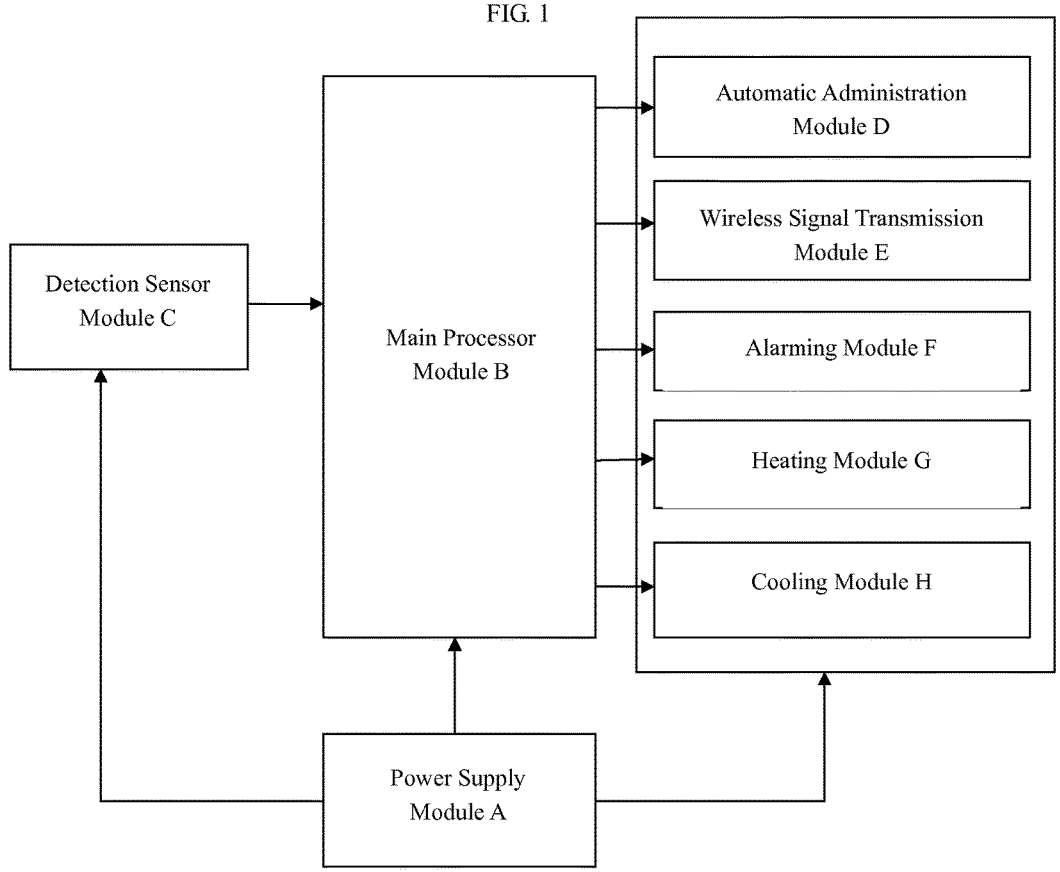
FIG. 2 is a flow chart of the basic principle of the second embodiment of the detection and therapeutic device according to the present invention.

FIG. 2 is a flow chart representing the basic principle of the second embodiment of the detection and therapeutic device according to the present invention.

As shown in the FIG. 2, the detection and therapeutic device interpreted in the second embodiment comprises a power supply module (a), a main processor module (b), a detection sensor module (c) and an automatic administration module (d), and functions, structures and technical solutions thereof are resemble with those of the first embodiment shown in FIG. 1. Apart from those above-identified structures, the detection and therapeutic device interpreted in the second embodiment further comprises multiple additional function modules so as to provide the detection and therapeutic device with extended functions.

More specifically, the additional function modules comprise a wireless signal transmission module (e) which is connected with the main processor module (b) and the power supply module (a) and used for receiving or sending wireless signals. The wireless signal transmission module is capable of sending out results generated by the sensors in the detection sensor module and receiving health guiding information. The wireless signal transmission module can be realized by adopting a blue-tooth transmission module or a mobile communication module and the like. Accordingly, results detected can be sent to targeted mobile phones and health guiding information sent by other mobile phones or medical centers can be received.

The alarming module (f) is connected with the main processor module (b) and the power supply module (a) and used for alarming or sending out emergency signals upon detecting risk factors for health. The alarming module (f) can be achieved by circuits functioned as audible and visual alarm. Sounds and emitted light of different colors or the sparkle of light can be produced for alarming to come to rescue.

The heating module (g) is connected with the main processor module (b) and the power supply module (a) and used for heating when users in need under the consideration of health. The heating module (g) can be achieved by tungsten filament heater, heating tubes and the like.

The cooling module (h) is connected with the main processor module (b) and the power supply module (a) and used for cooling when users in need under the consideration of health. The cooling module (h) can be achieved by condenser pipes.

Additionally, extended functional modules may further comprise a USB port module (not shown in the figures). The USB port module is capable of being connected with the main processor module (b) and/or the power supply module (a), so that data could be transmitted by the USB port module or the detection and therapeutic device could be powered by USB ports.

As shown in the FIG. 1 and the FIG. 2, the detection and therapeutic device can be independently and portably used, and also can be positioned in household goods as a part thereof so as to achieve detection and treatment when necessary. For example, the detection and therapeutic device can be positioned inside shoes to form remote monitoring shoes. Therefore, detection and effective and timely therapies can be achieved at any time and at any place by wearing the remote monitoring shoes.

In order to reduce energy consumption, the power supply module preferably adopts a self power-generating approach at work. Energy generated by walking can be used by the power supply module in the detection and therapeutic device.

Referring to the first embodiment of the power supply module of the detection and therapeutic device shown in the FIG. 3 to the FIG. 7, the structure and working principles of the embodiment are further explained as follows.

Figure 3:
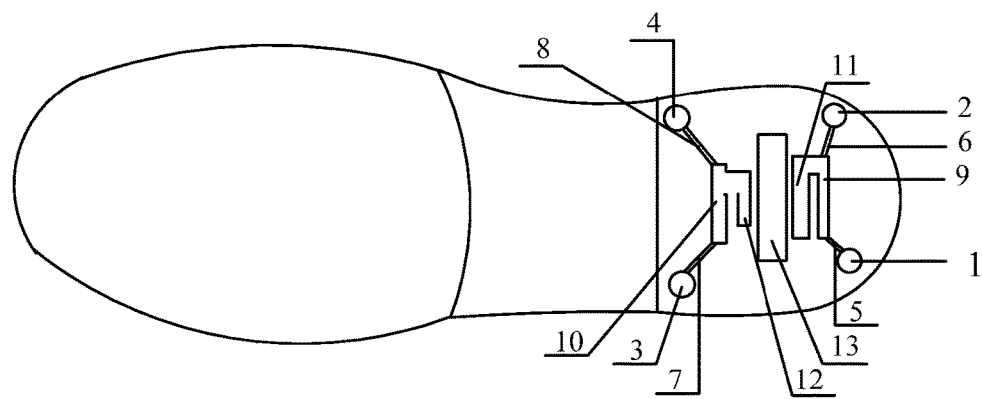
FIG. 3 is a schematic diagram of the overall structure of the power supply module in the remote monitoring shoes according to the present invention.

FIG. 3 is a schematic diagram of the overall structure of the power supply module in the remote monitoring shoes. As shown in the FIG. 3, the power supply modules are positioned in the shoe heels with comparatively large space and comprise self-generating power units and electrical energy storage units 13 which are connected with the self-generating power units. Each self-generating power unit comprises four stroke rods, two mechanical energy accumulators, two electrical generators and an electrical energy storage unit, which can be referred to a first stroke rod 1, a second stroke rod 2, a third stroke rod 3, a fourth stoke rod 4, a first mechanical energy accumulator 9, a second mechanical energy accumulator 10, a first electrical generator 11, a second electrical generator 12 and two rectifiers (not shown in the drawing) which are respectively connected with the two electrical generators. The first stroke rod (1) and the second stroke rod (2) are respectively drivingly connected with the first mechanical energy accumulator (9) through a first transmission shaft (5) and a second transmission shaft (6) and the third stroke rod (3) and the fourth stroke rod (4) are respectively drivingly connected with the second mechanical energy accumulator (10) through a third transmission shaft (7) and a fourth transmission shaft (8). The first mechanical energy accumulator (9) and the second mechanical energy accumulator (10) are respectively connected with a first electrical generator (11) and the second electrical generator (12). Energy produced by the first electrical generator (11) and the second electrical generator (12) and processed by the rectifiers can be used by modules in the remote monitoring shoes with electricity requirements, and also can be used for charging the electrical energy storage units 13, wherein the power outputs of the electrical energy storage units 13 are connected with other modules in the remote monitoring shoes with electricity requirements.

Figure 4:
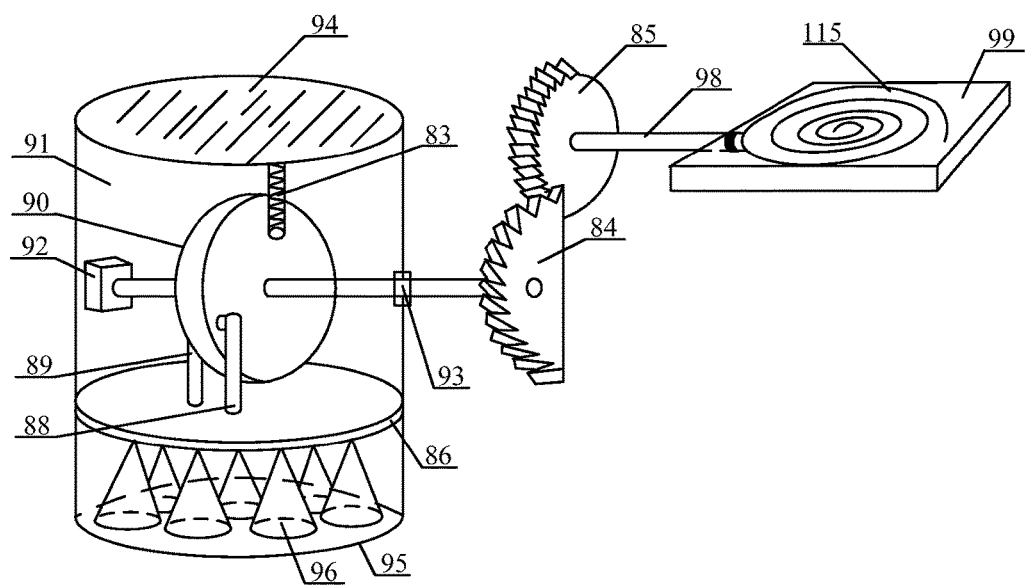
FIG. 4 is a schematic diagram of the assembling structure of the stroke rod and the mechanical energy accumulator in the power supply module shown in the FIG. 3.

In the implementation example, the assembling structure of the stroke rod and the mechanical energy accumulator can be achieved by using the structure shown in FIG. 4. As shown in the FIG. 4, any one of the stroke rods, from 1 to 4, comprises a rod body 91. A piston ring 86 and a stroke wheel 90 are arranged inside the rod body 91, wherein the piston ring 86 is perpendicular to the stroke wheel 90, the piston ring 86 is positioned on the middle and lower part of the rod body 91 and the stroke wheel 90 is arranged on the upper part of the piston ring 86. Gasbags 96 which drives the piston ring 86 to move vertically along the rod body 91 are arranged between the piston ring 86 and the bottom cap of the rod body 95. A bottom cap of the rod body 95 is made by elastic material, such as rubber and the gasbags 96 are capable of swelling or shrinking according to varied pressure so as to drive the piston ring 86 to move vertically. The piston ring 86 is hinged to the stroke wheel 90 by the connecting rod 88 and the connecting rod 89 and the top end of the stroke wheel 90 is connected with a top cap of the rod body 94 by a tension spring 83. A stroke wheel axle 93 penetrating through the rod body is arranged in the middle part of the stroke wheel 93, wherein one end of the stroke wheel axle 93 is embedded inside a groove 92 formed in the inner wall of the rod body 91 and the other end of the stroke wheel axle protrudes from the rod body 91 and provided with a ratchet wheel 84 of 180 degree.

Each mechanical energy accumulator comprises a box body 99, wherein two clockwork boxes are arranged on the lateral sides of the box body 99 (only one of the clockwork boxes is shown in the FIG. 4). Each clock work box is provided with a clockwork 115 and a transmission shaft 98, wherein the transmission shaft 98 is used as the energy input of the mechanical energy accumulator; one end of the transmission shaft 98 is arranged inside the box body 99 and fixedly connected with one end of the clockwork 115 and the other end of the transmission shaft 98 protrudes from the box body 99 and provided with a driven wheel 85 engaging with the ratchet wheel 84 positioned on the stroke wheel axle 93.

Figure 6:
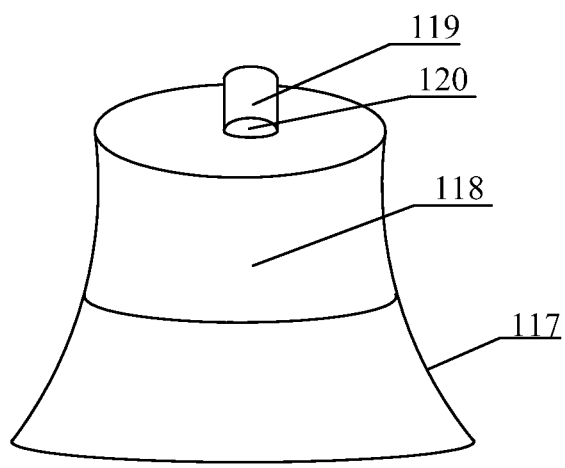
FIG. 6 is a schematic diagram of the gasbags in the stroke rod when the remote monitoring shoes are lifted.

Combined with the schematic diagram of FIG. 6 showing the structure of the gasbags 96 when the remote monitoring shoes are lifted, the working principles and processes of the collection of mechanical energy through the collaboration of the stroke rods and the mechanical energy accumulators in the embodiment are described as follows.

The remote monitoring shoes are lifted or lowered to contact with the ground alternatively during walking, and therefore kinetic energy could be produced by the movement of feet. As shoes are lifted, air in small gasbags 119 inside the gasbags of the stroke rods 96 are compressed into gasbag cavities 118 by pressure. Under this circumstance, the piston ring 86 is caused to fall toward the ground by the force of gravity so as to enable the stroke wheel 90 and the tension spring 83 to fall to the lowest point of one stroke. As the remote monitoring shoes contact with the ground, the force caused by body weight totally exerts on the shoe heels, and therefore, pressure inside the gasbag cavities rises significantly and the valve 120 for air inflow and air outflow, which is communicated with small gasbags 119 inside the gasbags serves as the only air output of the gasbag cavities 118 to release pressure. When air in the gas cavities 118 is compressed into the small gasbags 119, the inner walls of the small gasbags 119 are pressured so the small gasbags begin to swell. Accordingly, the piston ring 86 is driven by the swelling small gasbags 119 to move upward, so that the stroke wheel 90 is driven to roll by the connecting rods and the ratchet wheel 84 and the stroke wheel axle 98 are driven to roll by the stroke wheel 90, and hence, the mechanical rotational kinetic energy is produced. The transmission shaft is driven by the collaborative rotation of the ratchet wheel 84 and the driven wheel 85 and the energy can be locked in the mechanical energy accumulator by the clockworks.

Figure 7:
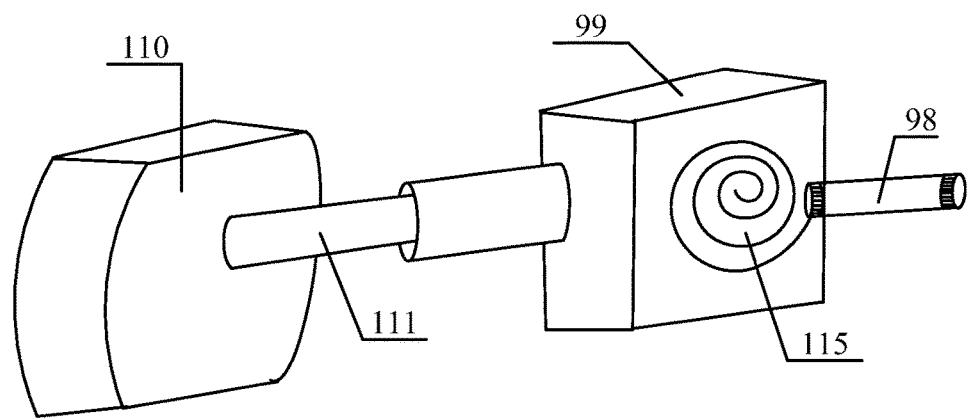
FIG. 7 is a schematic diagram of the structure of the mechanical energy accumulator and the electrical generator in the power supply module shown in the FIG. 3.

Referred to the schematic diagram of FIG. 7 showing the assembling structure of the mechanical energy accumulator and the electrical generator, the clockwork box of the mechanical energy accumulator is drivingly connected with the output shaft 111 of the mechanical energy accumulator through a gear-driven mechanism so that energy can be transferred to the electrical generator 110 through the output shaft. In this regard, mechanical energy can be transformed into electrical energy by the electrical generator and sent to the rectifier connected with the electrical generator 110.

Relying on the self-generating power unit with the above-identified structure and the regular movement in walking, the energy produced can be collected and stored, thereby transferring into electrical energy by the electrical generator so as to enable the modules to obtain electrical energy as required.

Figure 5:
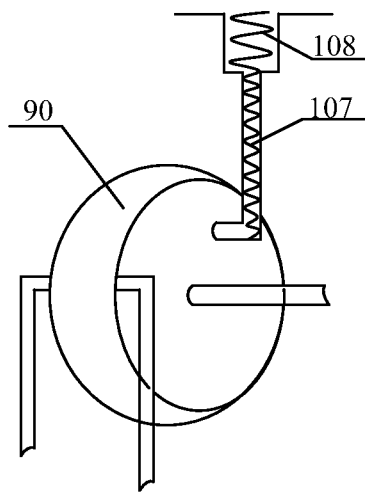
FIG. 5 is a schematic diagram of an alternative assembling structure of the stroke wheel and the tension spring which are arranged in the stroke rod shown in the FIG. 4.

Apart from the structure of an independent spring 83 shown in the FIG. 4, the tension spring connected with the stroke wheel 90 and the top cap of the rod body 94 in the stroke rods can be achieved with the assembling structure shown in the FIG. 5.

More specifically, as shown in the FIG. 5, the tension spring comprises two sections: an auxiliary spring 107 and a main spring 108 with varied elastic coefficients. One end of the main spring 108 is connected with the top cap of the rod body 94 and one end of the auxiliary spring is connected with the stroke wheel 90. According to these arrangements, the rotation of the stroke wheel can be performed more evenly so as to be beneficial to transmitting electrical energy in a constant and stable way.

A plurality of sensors can be arranged in the remote monitoring shoes according to needs in the described embodiments.

As shown in the FIG. 8, the sensors are disturbed inside the remote monitoring shoes in a structure described as follows.

A blood pressure sensor 27 and a pulse rate sensor 28 are arranged on the rear parts of the shoe uppers of the remote monitoring shoes and can be used for measuring the blood pressure and the pulse rate on the heels or at the arteries, and sending the results of measurement back to the main processor module inside the shoe heels for processing.

Five weight sensors for measuring body weight are respectively arranged inside the front shoe soles and the shoe heels and comprises a first weight sensor 35, a second weight sensor 36, a third weight sensor 37, a fourth weight sensor 38 and a fifth weight sensor 39. The front shoe soles are further provided with a body temperature sensor 64 for measuring the temperature of feet, a blood uric acid sensor 59, a blood glucose sensor 61, an antistreptolysin O sensor 60, a pH value sensor 62 and a protein sensor 63. Detection results can be obtained by testing secretions on the feet, such as skin dust, perspiration and the like by the sensors. Due to the facts that the structures and principles of the sensors at work are based on the prior art, no detailed interpretation concerning the sensors is included in this embodiment. Health indicators can be detected by the sensors at any place and at any time.

For example, the weight sensors supported by the power supply module, as shown in the FIG. 3 measure human body weight; the blood pressure sensor 27 and the pulse rate sensor 28 measure blood pressure and pulse rate on time according to the flow of blood in heel artery and convert the results to the main processor module. If the testing results are not beyond the presetting value in the main processor module, the blood pressure and the pulse rate is evaluated as being normal and the data is stored in the storage unit of the main processor module as a standby; if the testing results are irregular, the main processor sends alarming signals to particular mobile phones or first-aid station through the wireless signal transmission module to ensure that rescuers are informed timely. The temperature sensor 64 measure the temperature of feet on time; secretions on the feet, such as skin dust, perspiration and the like are tested by a blood uric acid sensor 59, a blood glucose sensor 61, an antistreptolysin O sensor 60, a pH value sensor 62 and a protein sensor 63 to acquire related health indicators. The data is converted to the main processor module and evaluated. If the testing result is irregular, acoustic or optical alarming signals are generated to warn the users or others of risk. In emergency, rescue medication, such as heart tonic pills, drugs to lower blood glucose and the like can be automatically administrated by the automatic administration module inside the shoe heels or shoe soles which are controlled by the main processor module; or the users can manually control the automatic administration module to inject medication for treatment or predication according to guide information from medical center.

Additionally, the remote monitoring shoes described in this embodiment are provided with infrared heating tubes on the front shoe soles corresponding to Yongquan acupuncture points. The infrared heating tube which is controlled by the main processor module is actuated to keep the Yongquan acupuncture point warm. Furthermore, in order to measure the walking distance and the number of steps of users to calculate exercises loads and other information, an infrared signal generator 32 and an infrared signal receiver 33 which are controlled by the main processor module are arranged on the inner side of each shoe uppers at interval, and particularly, the infrared signal generator 32 is positioned at the front end of the shoe upper and the infrared signal receiver 33 is mounted inside the shoe upper right above the shoe heel. The theoretical basis for utilizing the infrared signal generator and the infrared signal receiver to measure the walking distance and the number of steps is shown in the FIG. 15 and the FIG. 16 and the description thereof is shown as follows. In addition, USB ports may be provided at the shoes rear parts (not shown in drawings). Electric power can be supplied through the USB ports to the parts in the shoes in need of power. Remote data transmission between the remote monitoring shoes and USB devices may be realized through the USB ports.

The automatic injectors in the remote monitoring shoes can be achieved by varied structures according to different arrangements in the remote monitoring shoes.

Figure 9:
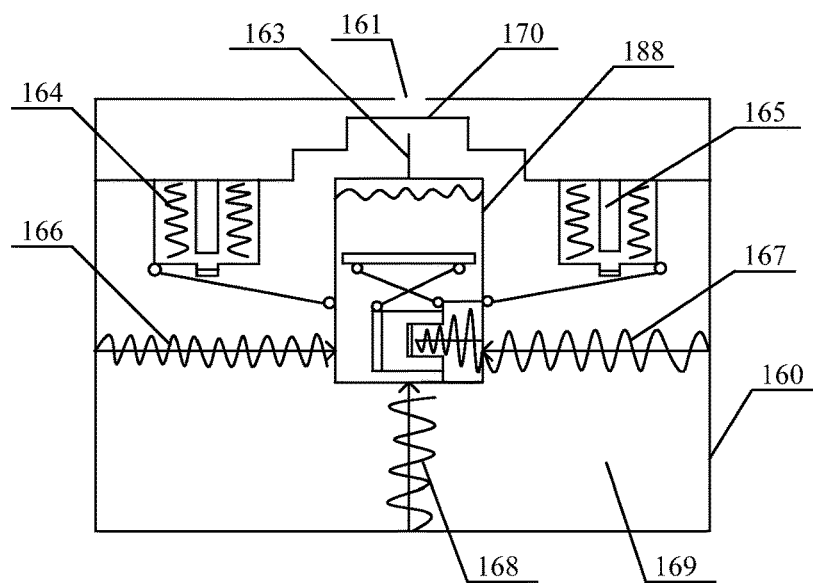
FIG. 9 is a schematic diagram of the structure of the first embodiment of the automatic injector in the remote monitoring shoes according to the present invention.
Figure 10:
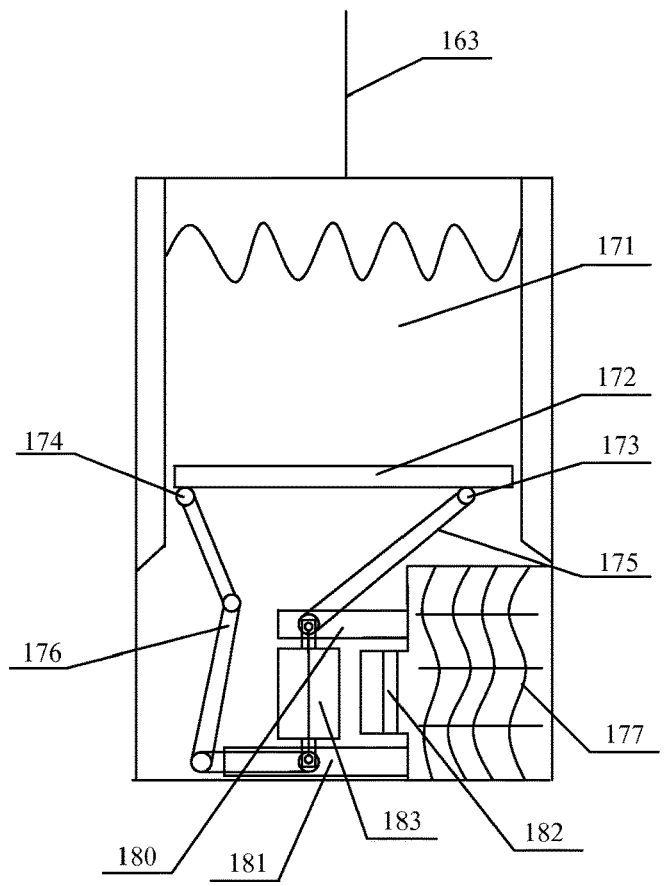
FIG. 10 is a schematic diagram of the syringe and the injection electromagnetic system in the automatic injector shown in the FIG. 9.
Figure 11:
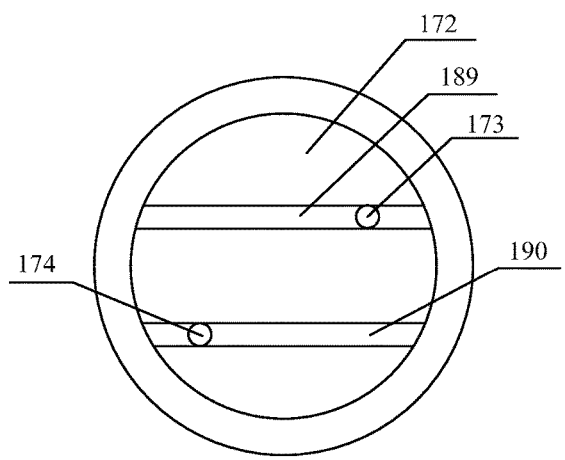
FIG. 11 is a schematic diagram of the bottom part of the propelled plate in the syringe shown in the FIG. 10.
Figure 12:
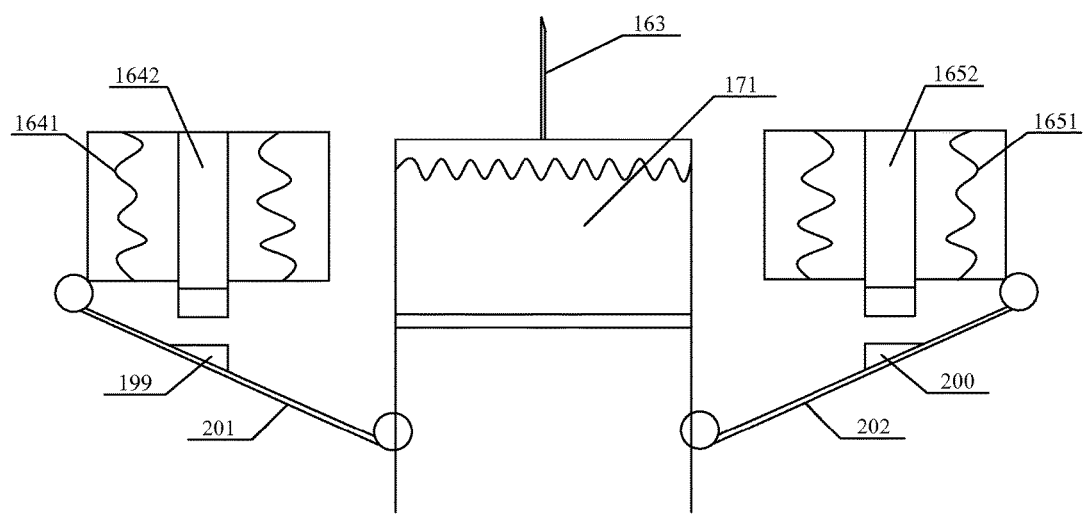
FIG. 12 is a schematic diagram of the displacement electromagnetic system and the syringe of the automatic injector shown in the FIG. 9.

The structure of the automatic injector in the remote monitoring shoes in the first embodiment can be shown in the FIG. 9, the FIG. 10, the FIG. 11 and the FIG. 12, wherein the FIG. 9 is a schematic diagram of the structure of the automatic injector, the FIG. 10 is a schematic diagram of the syringe and the injection electromagnetic system in the automatic injector, the FIG. 11 is a schematic diagram of the bottom part of the propelled plate in the syringe and the FIG. 12 is a schematic diagram of the displacement electromagnetic system and the syringe of the automatic injector.

As shown in the FIG. 9, the automatic injector in this embodiment comprises a shell 160, wherein a syringe 188 with an extruding needle 163 and a needle protective cover 170 are arranged inside the shell 160 and an orifice 161 corresponding to the needle 163 formed on the body of the shell 160. In order to position the overhung syringe 188, both sides of the lower part and the bottom end of the syringe 188 are respectively connected with a first retaining spring 166, a second retaining spring 167 and a third retaining spring 168 and the syringe 188 is connected with the inner wall of the shell 160 through the retaining springs. The syringe 188 is further provided with a first displacement electromagnetic system 164 and a second displacement electromagnetic system 165 which drive the syringe 188 to move toward the orifice 161 on the shell and detailed structure thereof is shown in the FIG. 12. A propelled plate, a cavity for injection and an injection electromagnetic system are arranged inside the syringe 188 and detailed structure thereof are shown in the FIG. 10 and the FIG. 11.

As shown in the FIG. 10 and the FIG. 11, the propelled plate 172 is arranged inside the syringe 188, wherein the cavity for injection 171 is formed between the end of the inner wall of the syringe with the needle 163 and one side of the propelled plate and used for containing injection in advance. The other side of the propelled plate, namely the bottom part of the propelled plate 172 is connected with an injection electromagnetic system used for driving the propelled plate to move.

A first propelled plate track 189 and a second propelled plate track 190 are arranged on the bottom part of the propelled plate 172. The injection electromagnetic system comprises an electromagnet 182 fixed on the inner wall of the syringe 188 and the iron core of the electromagnet 182 is wrapped by electromagnetic coils 177. The injection electromagnetic system further comprises iron 183 capable of attracting the iron core of the electromagnet according to the electrical current in the electromagnetic coils 177, a first iron track 180 and a second iron track 181 which allow the iron 183 slide transversely. One end of the iron 183 positioned on the first iron track 180 is hinged to one end of a first connecting rod mechanism 175 and the other end of the first connecting rod mechanism 175 rolls along the first propelled plate track 189; the other end of the iron 183 positioned on the second propelled plate track 181 is hinged to one end of the second connecting rod mechanism 176 and the other end of the second connecting rod mechanism 176 rolls along the second propelled plate track 190. In this embodiment, the first connecting rod mechanism 175 comprises a connecting rod and the second connecting rod mechanism 176 consists of a plurality of connecting rods.

The detailed structure of the displacement electromagnetic system is shown in the FIG. 12 and the displacement electromagnetic system comprises two sub systems which are respectively arranged on both sides of the syringe 188. The left sub system 164 comprises an electromagnet 1642 arranged on the shell 160 and the iron core of the electromagnet 1642 is wrapped by the electromagnetic coils 1643. An attracting arm 201 is positioned below the electromagnet 1642, wherein one end of the attracting arm 201 is hinged to the electromagnet 1642 and the other end of the attracting arm 201 is hinged to the syringe 188. On the attracting arm 201, there is provided at a position corresponding to the iron core of the electromagnet 1642 an iron 199 capable of attracting the iron core of the electromagnet 1642 according to the electrical current in the electromagnetic coils 1641. The structure of the right sub system 165 resembles the left sub system and the right sub system comprises an electromagnet 1652 arranged on the shell 160 and the iron core of the electromagnet 1652 is wrapped by the electromagnetic coils 1653. An attracting arm 202 is positioned below the electromagnet 1652, wherein one end of the attracting arm 202 is hinged to the electromagnet 1652 and the other end of the attracting arm 200 is hinged to the syringe 188. An iron 200 capable of attracting the iron core of the electromagnet 1652 according to the electrical current in the electromagnetic coils 1651 is arranged on the attracting arm 202 corresponding to the electromagnet 1652.

The working principle and process of the automatic injector is described as follows. Under a non-injecting mode, the displacement electromagnetic system and the electromagnetic coils of the injection electromagnetic system are not energized and the structure of the overall automatic injector is shown in the FIG. 9. If action of injection is needed, the displacement electromagnetic systems and the electromagnetic coils of the injection electromagnetic system are energized. At this point, magnetic force is produced by the electromagnet 1642 and the electromagnet 1652 to respectively attract the iron 199 and the iron 200 below so as to enable the syringe 188 to move vertically under the action of the left attracting arm 201 and the right attracting arm 202. Accordingly, the needle 163 is capable of piercing the needle protective cover 170 and protruding from the orifice 161 to stab skin on the feet. In the meanwhile, a magnetic force for attracting the iron 183 is produced by the electromagnet 182 in the injection electromagnetic system to enable the iron 183 to move to the right side along the first iron track 180 and the second iron track 182. Under this circumstance, the first connecting rod mechanism 175 and the second connecting rod mechanism 176 are driven to push the propelled plate 172 to move upward, so that injection in the cavity 171 is administrated by the needle 163 into the feet. Therefore, automatic administration is realized.

Upon the completion of administration, power supply to the electromagnetic systems and the electromagnetic coils of the injection electromagnetic system are cut off and magnetic properties of the electromagnets disappear. The attracting arm 201 and the attracting arm 202 in the displacement electromagnetic systems move downwards to drive the syringe 188 to move down, so as to enable the needle 163 to move back to the needle protective cover 163. In the meanwhile, the iron 183 move towards the left side along the first iron track 180 and the second iron track 182 and the propelled plate 172 is pulled down through the movement of the first connecting rod mechanism 175 and the second connecting rod mechanism 176 so as to enable the automatic injector to return to the status of non-injection shown in the FIG. 9.

The automatic injector with the above-identified structure is capable of being arranged inside the shoe heels with comparatively larger space to administrate injection for stabilizing blood sugar levels.

Figure 13:
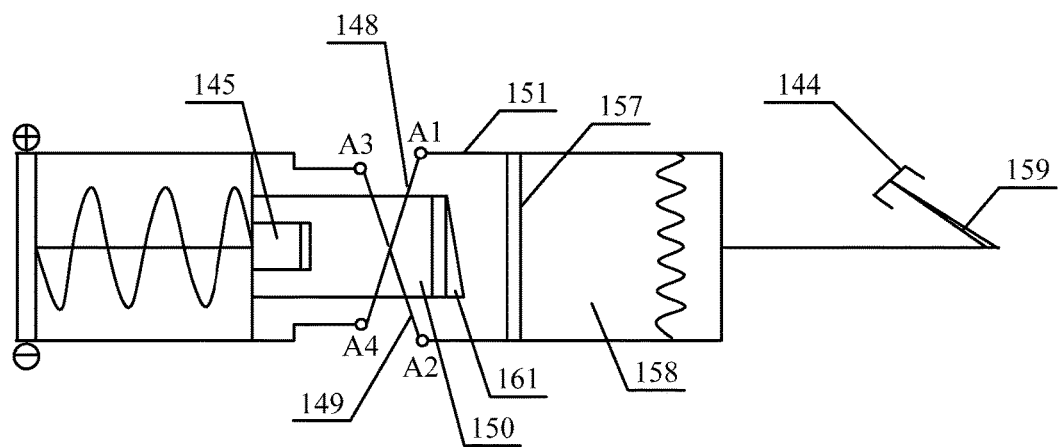
FIG. 13 is a schematic diagram of the second embodiment of the automatic injector in the remote monitoring shoes in the status of being not used according to the present invention.
Figure 14:
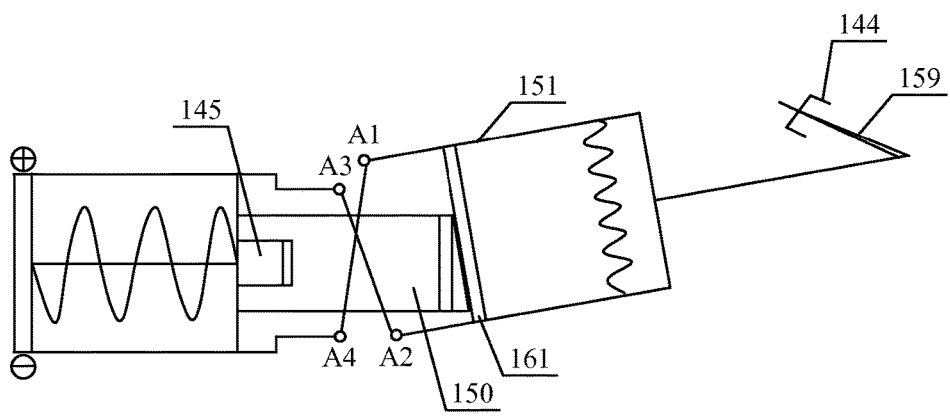
FIG. 14 is a schematic diagram of the automatic injector shown in the FIG. 13 in the status of injection.

The second embodiment of the automatic injector is shown in the FIG. 13 and the FIG. 14, wherein the FIG. 13 is a schematic diagram of the automatic injector being out of use and the FIG. 14 is a schematic diagram of the automatic injector in a status of administration.

As shown in the FIG. 13, the automatic injector comprises a syringe 151, wherein a propelled plate 157 is arranged inside the syringe. A hook-shaped needle 159 is positioned at the front end of the syringe 151 and a needle protective cover 144 is positioned at the front end of the needle in a sleeved manner. A cavity is formed between the propelled plate 157 and one side of the inner wall of the syringe 151 with the hook-shaped needle 159 and used for containing the injection for administrating. The automatic injector further comprises an injection electromagnetic system which is used for driving the propelled plate 157 and the syringe 151 to move obliquely so as to enable the hook-shaped needle 159 to hook backwards and pierce into skin. The injection electromagnetic system comprises a fixed electromagnet 145 and a moving electromagnet 150 which are wrapped by electromagnetic coils. Both ends of the fixed electromagnet 145, namely A3 and A4 are respectively hinged to both ends of the syringe 151, namely A2 and A1, which are away from the tail end of the hook-shaped needled by connecting rods. To be specific, A4 is hinged to A1 through a first connecting rod 148 and A3 is hinged to A2 through a second connecting rod 149. The iron core of the moving electromagnet 150 covers the iron core of the fixed electromagnet 145 and moves along the moving direction of the propelled plate 157 inside the syringe. The front end of the iron core of the moving electromagnet 150 is an inclined plane 161. The direction of the tilt is matched with the oblique moving direction of the propelled plate 157 and the syringe 151 as the iron core of the moving electromagnet 150 moves toward and contacts with the propelled plate 157 to enable the hook-shaped needle 159 to hook backwards and pierce into skin.

The working principle of the automatic injector with the above-mentioned structure is interpreted as follows.

When the automatic injector is not in the injection mode, the electromagnetic coils of the injection electromagnetic system are not powered and the moving electromagnet 150 and the fixed electromagnet 145 are at rest correspondingly. The status of the overall automatic injector is shown in the FIG. 13. If administration is needed, the electromagnetic coils of the injection electromagnetic system are energized. Repulsive forces produced by the fixed electromagnet 145 and the moving electromagnet 150 to enable the moving electromagnet 50 to move to the right side and contact with the propelled plate 157. Due to the fact that the front end of the propelled plate 157 is the inclined plane 161, the propelled plate 157 and the syringe 151 are tilted upward by the strong pulling force exerted by the propelled plate as shown in the FIG. 14. At this point, the hook-shaped needle 159 hooks backwards and pierces out of the needle protective cover into skin. Therefore, injection in the cavity 158 is administrated into human body by the movement of the propelled plate 157.

Upon completion of injection, power supply to the electromagnetic coils of the injection electromagnetic system is cut off and the moving electromagnet moves to the left side. The overall syringe 151 and the propelled plate 157 return to the status shown in the FIG. 13 and the hook-shaped needle 159 returns back to the needle protective cover 144.

The automatic injector described in the second embodiment can be arranged inside the front shoe soles for administrating heart tonic injection.

Figure 15:
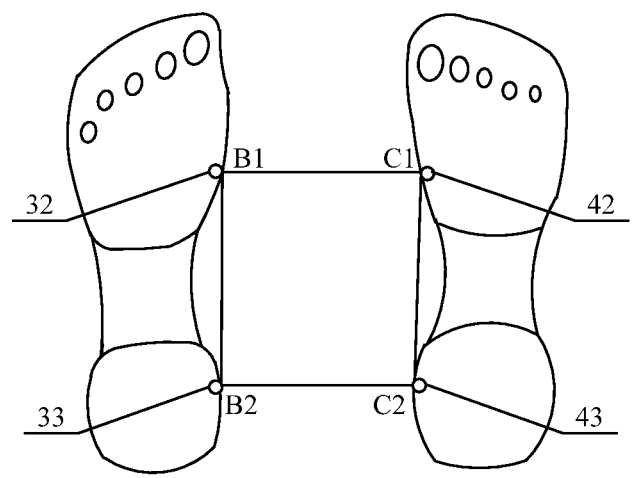
FIG. 15 is the first schematic diagram representing the basic principle for measuring walking steps of the remote monitoring shoes according to the present invention.
Figure 16:
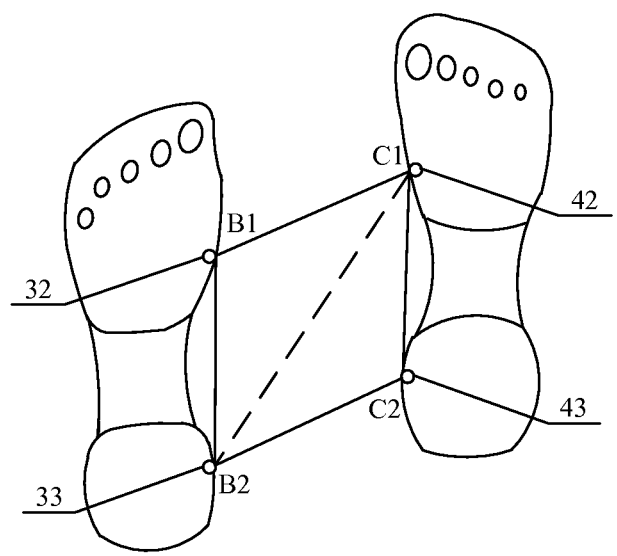
FIG. 16 is the second schematic diagram representing the basic principle for measuring walking steps of the remote monitoring shoes according to the present invention.

The FIG. 15 and FIG. 16 are schematic diagrams of the theoretical basis for measuring walking distance with the remote monitoring shoes.

Figure 8:
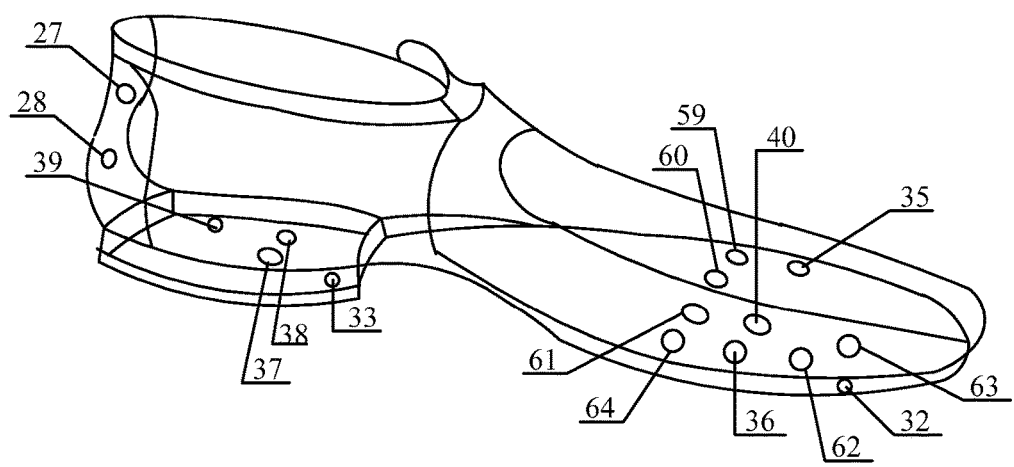
FIG. 8 is a schematic diagram showing the configuration of the sensors and the distribution thereof in the remote monitoring shoes according to the present invention.

As shown in the FIG. 8, the FIG. 15 and the FIG. 16, an infrared signal generator 32 is arranged at the front part of the inner part of the left shoe upper and an infrared signal receiver 33 is positioned inside the shoe upper approaching the left shoe heel; an infrared signal generator 42 is arranged at the front part of the inner part of the right shoe upper and an infrared signal receiver 43 is positioned inside the shoe upper approaching the right shoe heel. In particular, the infrared signal receiver 33 is merely used for receiving signals produced by the infrared signal generator 42 and the infrared signal receiver 43 is merely used for receiving signals produced by the infrared signal generator 32. The infrared signal generator 32, the infrared signal receiver 33, the infrared signal generator 42 and the infrared signal receiver 43 are respectively connected with the main processor module. As shown in the drawings, when two feet draws close to each other, the points of positions of the infrared signal generator 32, the infrared signal receiver 33, the infrared signal generator 42 and the infrared signal receiver 43 can be connected as a rectangle; when one foot steps forward, the points of positions of the infrared signal generator 32, the infrared signal receiver 33, the infrared signal generator 42 and the infrared signal receiver 43 can be connected as a rhombus. Accordingly, the main processor module can read data on signals produced and received by the infrared generators and receivers and measure distance of each step and calculate the sum of steps according to preset algorithms. Furthermore, information presenting the evaluation results of vital signs, such as exercise loads and the like can be obtained by the main processor. Detailed working principles and calculating methods can be referred to the prior art, thereby not being explained here.

In order to measure blood pressure and pulse rate conveniently, a telescopic mechanism is arranged at the rear parts of shoe uppers corresponding to the ankle artery. Gasbags are connected with the telescopic mechanism and provided with a blood pressure sensor 27 and a pulse rate sensor 28. Actions of the gasbags to press against or release the ankle artery can be achieved by the telescopic movement of the telescopic mechanism, so as to prevent blood in artery from flowing smoothly at intervals for measuring blood pressure and pulse rate by the blood pressure sensor 27 and the pulse rate sensor 28 on the gasbags.

Figure 17:
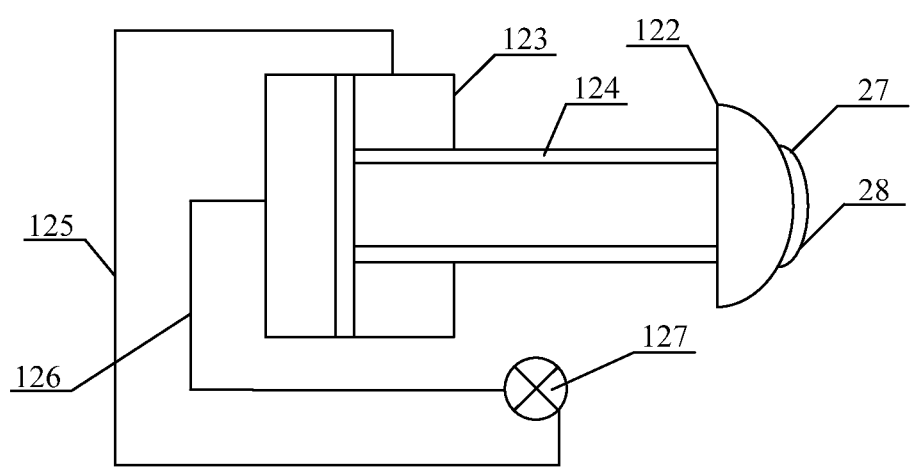
FIG. 17 is a schematic diagram of the structure for measuring blood pressure and pulse rate by the remote monitoring shoes in a specified embodiment according to the present invention.

The structure for measuring blood pressure and pulse rate by the remote monitoring shoe in an embodiment is shown in the FIG. 17.

As shown in the FIG. 17, the telescopic mechanism is achieved by a hydraulic system. To be specific, the telescopic mechanism comprises a hydraulic cylinder 123 and a hydraulic pump 127, the cylinder body of the hydraulic cylinder 123 is connected with the hydraulic pump 127 by a hydraulic tube 125. One end of a piston rod 124 of the hydraulic cylinder 123 thereon is connected with a gasbag 122 in a rigid manner and the front end of the gasbag 122, namely the end back to the piston rod 124 is provided with the blood pressure sensor 27 and the pulse rate sensor 28. The hydraulic cylinder 123 is divided into two cavities by the piston rod inside and each cavity is communicated with the hydraulic pump 127 through a hydraulic tube.

The continuous service of the hydraulic pump 123 is controlled by the main processor module inside the remote monitoring shoes. The flow direction of hydraulic oil in the hydraulic pump 123 can be changed by the hydraulic pump flow direction, so as to enable the hydraulic oil to flow from one cavity to another in the hydraulic cylinder for keeping the piston rod 124 moving in a horizontal and reciprocating manner. When the piston rod 124 moves to the right side, the gasbag 122 is pressed against the ankle artery to prevent blood from flowing smoothly; when the piston rod 124 move to the left side, the ankle artery is released due to the fact that the gasbag is in a status without being pressed and the smooth blood flow in the ankle artery restores.

Measurement of blood pressure and pulse rate can be achieved by detecting the status of blood flow in the ankle artery through the blood pressure sensor 27 and the pulse rate sensor 28, detection signals are sent back to the main processor module to obtain blood pressure and pulse rate. Therefore, on-time detection of blood pressure and pulse rate can be achieved by the control of the hydraulic pump 127.

According to this arrangement, the overall size of the telescopic mechanism is small and the structure is simple and easy to control, thereby being perfectly applicable to being used inside shoes.

The above-identified embodiments are instructions of the technical solutions presented in the invention rather than the restriction of the scope of protection. Technicians in the field are capable of modifying the technical solutions referring to the embodiments or equivalently replacing part of the technical features although a detailed interpretation of the invention are presented in the embodiments. But the invention and the scope of protection thereof are not changed by the matter of modification and replacement.

The invention claimed is:

1. A detection and therapeutic device characterized in that the detection and therapeutic device comprises
    a power supply module which is connected with modules with electricity need and which is used for powering the modules with electricity need,
    a main processor module which is used for collecting and processing signals from a plurality of sensors and controlling working status of an automatic injector module,
    a detection sensor module which comprises the plurality of sensors in connection with the main processor module and is used for examining nerves, organs or secretions and sending back results from examining the nerves organs or secretions to the main processor module,
    an automatic administration module which comprises a plurality of automatic injectors in connection with the main processor module and is used for administrating automatically according to signals for controlling from the main processor module;
    wherein the power supply module comprises a self-generating power unit and an electrical energy storage unit which is connected with the self-generating power unit; the modules with electricity need of the detection and therapeutic device are respectively connected with a power output of the self-generating power unit and a power output of the electrical energy storage unit;
    wherein the self-generating power unit comprises a plurality of stroke rods, a plurality of mechanical energy accumulators which are drivingly connected with the stroke rods, electrical generators which are connected with the mechanical energy accumulators and a rectifier which is connected with the electrical generators; and
    wherein each of the stroke rods comprises a rod body, wherein a piston ring and a stroke wheel are arranged inside the rod body; a first gasbag which is used for driving the piston ring to move vertically along the rod body is positioned between the piston ring and a bottom cap of the rod body, wherein the piston ring is hinged to the stroke wheel by connecting rods; a top cap of the rod body is connected with a top end of the stroke wheel by a tension spring and a stroke axle penetrating through the rod body is arranged in a middle part of the stroke wheel; one end of the stroke axle is embedded inside a groove formed in the rod body and the other end of the stroke axle protrudes from the rod body and is provided with a ratchet wheel; each of the mechanical energy accumulators comprises a box body, wherein clockwork boxes provided with a clockwork and a transmission shaft are arranged on lateral sides of the box body; the transmission shaft is used as a power input of the mechanical energy accumulator, wherein one end of the transmission shaft is positioned inside the box body and the other end of the transmission shaft protrudes from the box body and provided with a driven wheel engaging with a ratchet wheel arranged on the stroke axle; the clockwork box is drivingly connected with an output shaft of the mechanical energy accumulator by the gear transmission mechanism, so as to transmit power to the electrical generators through the output shaft; electrical energy is configured to be sent to the rectifier after being transformed from mechanical energy by the electric generators; and wherein the modules with electricity need comprises the main processor module, the detection sensor module, and the automatic administration module.

2. The detection and therapeutic device according to the claim 1 characterized in that the detection and therapeutic device further comprises a wireless signal transmission module which is connected with the main processor module and the power supply module and used for receiving and sending signals, wherein the modules with electricity need further comprises the wireless signal transmission module.

3. The detection and therapeutic device according to the claim 1 characterized in that the detection and therapeutic device further comprises an alarming module, a heating module and/or a cooling module which are connected with the main processor module and the power supply module, and wherein the modules with electricity need further comprises the alarming module, the heating module and the cooling module.

4. The detection and therapeutic device according to claim 1 characterized in that the plurality of sensors comprises at least one sensor selected from a weight sensor, a body temperature sensor, a blood pressure sensor, a pulse rate sensor, a blood uric acid sensor, a blood glucose sensor, an antistreptolysin O sensor, a pH value sensor and a protein sensor.

5. The detection and therapeutic device according to the claim 4 characterized in that the detection and therapeutic device comprises a second gasbag and a telescopic mechanism which is connected with the second gasbag, wherein the at least one sensor is selected as the blood pressure sensor and the pulse rate sensor, the blood pressure sensor and the pulse rate sensor are configured to be positioned on the second gasbag.

6. The detection and therapeutic device according to the claim 5 characterized in that the telescopic mechanism comprises a hydraulic cylinder, wherein a piston rod of the hydraulic cylinder and the second gasbag are in a rigid connection and a hydraulic pump is connected with a cylinder body of the hydraulic cylinder.

7. The detection and therapeutic device according to claim 1 characterized in that each of the automatic injectors comprises a shell, wherein a syringe with an extruding needle and a needle protective cover are arranged inside the shell and an orifice is formed at a position of the needle; the syringe is connected with an inner wall of the shell by retaining springs; a displacement electromagnetic system which is used for driving the syringe to move to the orifice is positioned on the syringe; a propelled plate is arranged inside the syringe and a cavity for injection is formed between an end of the inner wall of the syringe with the needle and one side of the propelled plate, and the other side of the propelled plate is connected with an injection electromagnetic system which is used for driving the propelled plate to move.

8. The detection and therapeutic device according to claim 7 characterized in that the displacement electromagnetic system comprises two sub systems, wherein the two sub systems are respectively arranged on both sides of the syringe; each of the sub systems comprises a first electromagnet arranged on the shell and an iron core inside the first electromagnet is wrapped by electromagnetic coils; an attracting arm is positioned below the first electromagnet, wherein one end of the attracting arm is hinged to the first electromagnet and the other end of the attracting arm is hinged to the syringe; a first iron capable of attracting the iron core of the first electromagnet according to the electrical current in the electromagnetic coils arranged on the attracting arm corresponding to the position of the iron core;

a first propelled plate track and a second propelled plate track are arranged on the side of the propelled plate back against the cavity for injection; the injection electromagnetic system comprises a second electromagnet fixed on the inner wall of the syringe and an iron core of the second electromagnet is wrapped by electromagnetic coils wrapped on the second electromagnet; the injection electromagnetic system further comprises a second iron capable of attracting the iron core of the second electromagnet according to the electrical current in the electromagnetic coils and a first iron track and a second iron track which enable the second iron to slide; one end of the second iron positioned on the first iron track is hinged to one end of a first connecting rod mechanism, the other end of the first connecting rod mechanism rolls along the first propelled plate track through a first rolling wheel; the other end of the second iron positioned on the second iron track is hinged to one end of a second connecting rod mechanism, the other end of the second connecting rod mechanism rolls along the second propelled plate track through a second rolling wheel.

9. The detection and therapeutic device according to claim 1 characterized in that each of the automatic injectors comprises a syringe, a propelled plate arranged inside the syringe, a hook-shaped needle positioned at a front end of the syringe and a cavity for injection is formed between the propelled plate and an end of the inner wall of the syringe with the hook-shaped needle; the automatic injector further comprises an injection electromagnetic system capable of driving the propelled plate and the syringe to move obliquely so as to enable the hook-shaped needle to retreat backwards; the injection electromagnetic system comprises a fixed magnet and a moving magnet which are respectively wrapped by electromagnetic coils, wherein both ends of the fixed magnet are respectively hinged to both ends of the syringe away from a tail end of the hook-shaped needle by connecting rods; an iron core of the moving magnet covers an iron core of the fixed magnet and moves along the moving direction of the propelled plate inside the syringe and a front end of the moving magnet is an inclined plane which is configured to tilt the propelled plate and the syringe upon the iron core of the moving magnet moving towards the propelled plate and contacting with the propelled plate.

10. A remote monitoring shoe comprises a shoe heel, a front shoe sole, a shoe upper and a vamp and is characterized in that the detection and therapeutic device according to claim 1 is arranged inside the remote monitoring shoe; the power supply modules and the main processor modules of the detection and therapeutic device are arranged inside the shoe heel and the plurality of sensors are positioned dispersedly inside the shoe heel, the front shoe sole and the shoe upper; the automatic injectors are dispersedly arranged inside the shoe heel and the front shoe sole and the shoe heel are further provided with wireless signal transmission modules respectively connected with the main processor modules and the power supply modules, wherein the modules with electricity needs further comprises the wireless signal transmission modules.

11. The remote monitoring shoe according to the claim 10 characterized in that the shoe heel is further provided with alarming modules connected with the main processor modules and the power supply modules, so as to alarm the users upon potential risk factors for health detected; the front shoe sole is further provided with heating modules connected with the main processor modules and the power supply modules; the shoe upper is further provided with cooling modules connected with the main processor modules and the power supply modules so as to enable the user to lower body temperature or keep warm as required; wherein the modules with electricity needs further comprises the alarming modules, the heating modules and the cooling modules.

12. The remote monitoring shoe according to claim 10 characterized in that the remote monitoring shoe is provided with weight sensors inside the shoe heel and the front shoe sole, body temperature sensors, blood uric acid sensors, blood glucose sensors, antistreptolysin O test sensors, pH value sensors and protein sensors inside the front shoe sole and blood pressure sensors and pulse rate sensors on back ends of the shoe upper which corresponds to an ankle artery.

13. The remote monitoring shoe according to claim 12 characterized in that the second gasbag and telescopic mechanisms connected with a second gasbag are positioned at a rear end of the shoe upper, and wherein when blood pressure sensors and pulse rate sensors are provided, the blood pressure sensors and the pulse rate sensors are arranged on the second gasbag.

14. The remote monitoring shoe according to claim 13, characterized in that each of the telescopic mechanisms comprises a hydraulic cylinder, wherein a piston rod of the hydraulic cylinder and the second gasbag are in a rigid connection and a hydraulic pump is connected with the cylinder body of the hydraulic cylinder.

15. The remote monitoring shoe according to claim 10 characterized in that the automatic injectors are arranged inside the shoe heel and the automatic injector comprises a shell, wherein a syringe with an extruding needle and a needle protective cover are arranged inside the shell and an orifice formed at the position of the needle; the syringe is connected with an inner wall of the shell by retaining springs and displacement electromagnetic systems which are used for driving the syringe to move to the orifice are positioned on the syringe; a propelled plate is arranged inside the syringe and a cavity for injection is formed between the end of the inner wall of the syringe with the needle and one side of the propelled plate, and the other side of the propelled plate is connected with an injection electromagnetic system used for driving the propelled plate to move.

16. The remote monitoring shoe according to claim 15 characterized in that each displacement electromagnetic system comprises two sub systems; each sub system is respectively arranged on one side of the syringe and comprises a first electromagnet arranged on the shell and an iron core inside the first electromagnet is wrapped by electromagnetic coils; an attracting arm is positioned below the first electromagnet, wherein one end of the attracting arm is hinged to the first electromagnet and the other end of the attracting arm is hinged to the syringe; a first iron capable of attracting the iron core of the first electromagnet according to the electrical current in the electromagnetic coils is arranged on the attracting arm corresponding to the position of the iron core;

a first propelled plate track and a second propelled plate track are arranged on the side of the propelled plate back against the cavity for injection; the injection electromagnetic system comprises a second electromagnet fixed on the inner wall of the syringe and an iron core of the second electromagnet is wrapped by electromagnetic coils wrapped on the second electromagnet; the injection electromagnetic system is further comprises a second iron capable of attracting the iron core of the second electromagnet according to the electrical current in the electromagnetic coils, a first iron track and a second iron track which enable the second iron to slide; one end of the second iron positioned on the first iron track is hinged to one end of a first connecting rod mechanism, the other end of the first connecting rod mechanism rolls along the first propelled plate track through a first rolling wheel; the other end of the second iron positioned on the second iron track is hinged to one end of a second connecting rod mechanism, the other end of the second connecting rod mechanism rolls along the second propelled plate track through a second rolling wheel.

17. The remote monitoring shoe according to claim 15 characterized in that each automatic injector is arranged inside the front shoe sole and comprises a syringe, a propelled plate arranged inside the syringe, a hook-shaped needle positioned at a front end of the syringe and a cavity for injection is formed between the propelled plate and an end of the inner wall of the syringe with the hook-shaped needle; the automatic injector further comprises an injection electromagnetic system capable of driving the propelled plate and the syringe to move obliquely so as to enable the hook-shaped needle to retreat backwards; the injection electromagnetic system comprises a fixed magnet and a moving magnet which are respectively wrapped by electromagnetic coils, wherein both ends of the fixed magnet are hinged to both ends of the syringe away from a tail end of the hook-shaped needle by connecting rods; an iron core of the moving magnet covers an iron core of the fixed magnet and moves along the moving direction of the propelled plate inside the syringe and a front end of the moving magnet is an inclined plane which is configured to tilt the propelled plate and the syringe upon the iron core of the moving magnet moving towards the propelled plate and contacting with the propelled plate.

18. The remote monitoring shoe according to claim 10 characterized in that infrared signal generators and infrared signal receivers which are connected with the main processor modules are arranged on inner sides of the shoe upper at intervals.

\* \* \* \* \*